United States Patent [19]

Eisenberg et al.

[11] Patent Number: 5,527,797

[45] Date of Patent: Jun. 18, 1996

[54] PROCESS FOR TRANSPORT OF AGENTS ACROSS THE SKIN AND COMPOSITIONS AND ARTICLES USEFUL THEREIN

[75] Inventors: Solomon R. Eisenberg, Newton, Mass.; Carlos M. Samour, Newport, R.I.

[73] Assignees: Macrochem Corporation, Lexington; The Trustees of Boston University, Boston, both of Mass.

[21] Appl. No.: 109,599

[22] Filed: Aug. 20, 1993

Related U.S. Application Data

[63] Continuation of Ser. No. 823,380, Jan. 21, 1992, abandoned.

[51] Int. Cl.⁶ .................... A61K 31/535; A61K 31/17; A61K 31/045
[52] U.S. Cl. ................ 514/231.2; 514/588; 514/724
[58] Field of Search ................ 514/231.2, 588, 514/724

[56] References Cited

U.S. PATENT DOCUMENTS 4,861,764  8/1989  Samour et al. .................. 514/177

*Primary Examiner*—Zohreh Fay
*Attorney, Agent, or Firm*—Sherman and Shalloway

[57] ABSTRACT

New and improved method for the transdermal administration of agents is provided utilizing iontophoresis in conjunction with a water-insoluble, stratum corneum-lipid modifier. The lipid modifier may be used prior to iontophoresis or simultaneously therewith. The lipid modifier may be selected from a wide variety of moieties of the general formula R—X where R is a $C_5$ to $C_{28}$ alkyl or unsaturated alkyl and X is a member of the following: 1,3-dioxane; 1,3-dioxolane; lactam; morpholine; —COOH; —OH; —COOR'; —C—N(R')$_2$; cyclo ethylene and propylene carbonates; —CONH$_2$; —(CH$_2$—CH$_2$O)$_n$H;

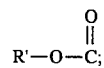

acetals, and hemiacetals; and wherein R' is lower alkyl (e.g., $C_1$ to $C_3$) and n is an integer of from 1 to 20. Optionally there may be present a polar, water-soluble chemical compound from the group of alcohols, glycols, lactams, dioxolanes, esters, ureas, morpholine and the like. Compositions and articles useful in the processes of the present invention are also provided.

20 Claims, 11 Drawing Sheets

PROCESS FOR TRANSPORT OF AGENTS ACROSS THE SKIN AND COMPOSITIONS AND ARTICLES USEFUL THEREIN

This is a continuation of application Ser. No. 07/823,380 filed Jan. 21, 1992 now abandoned.

This invention relates to new and improved methods for transporting ingredients including pharmaceuticals utilizing iontophoresis in conjunction with a stratum corneum-lipid modifier, and compositions and articles useful in such methods.

BACKGROUND OF THE INVENTION

It is well known that many compounds have the capacity more or less for entering the subdermal layers of the skin eventually into the host's circulatory system. This process is said to be a passive penetration process. The major focus for the transdermal mode of treatment lies in the non-invasiveness thereof which obviates parenteral administration and its obvious disadvantages as well as the disadvantages attendant with the oral mode of administration such as gastrointestinal distress and the breakdown of the active ingredient due to metabolic and/or digestive processes. Generally the passive penetration activity of most active ingredients is not sufficient for most clinical purposes.

The durability of the delivery of physiologically active agents through the skin, i.e., transdermally, as opposed to other methods or parenteral administration or via the digestive system is based on many factors. The large surface area of the skin (about 1.8 sq. meters for the average adult man) and the large circulatory (about one-third of total body blood) and lymphatic networks available near the skin, the generally non-invasive nature of topical applications and their delivery through the skin, the convenience, the safety, the potential greater control of delivered agents, and the minimal side effects are just some of the advantages seen for this technique.

While not every and all agents may be suitable for transdermal delivery because of local irritation, allergic reactions, etc. most are indicated as suitable but, unfortunately, the greatest problem is overcoming the general barrier to drug penetration (or indeed to any material) of the skin. A drug must pass through the outer layer of skin or epidermis and into the dermis layer before being absorbed into the blood stream. The epidermis comprises two main parts, the stratum corneum and the stratum germinativum. The stratum corneum forms the outermost layer of the epidermis and consists of many stratified layers of compacted, flattened, keratinized cells which have lost their nuclei. This outermost layer serves as a physical barrier to percutaneous absorption. Because of the barrier effect of the skin, it has heretofore only been possible to deliver drugs that are "low-dose" drugs, in the range of 10 mg/day or less, or those of low molecular weight. In addition they have to have the proper lipophilic-hydrophilic balance to permit adequate absorption. It was recognized as early as the beginning of this century that lipid-soluble substances such as nonelectrolytes have a comparatively greater skin permeability than water-soluble substances, such as electrolytes.

The phenomenon of percutaneous absorption or transdermal permeation can be viewed as a composite of a series of steps in sequence, that is, adsorption of a penetrant molecule onto the surface layers of the stratum corneum, diffusion through it and through the viable epidermis, and finally through the capillary dermis and into the microcirculation.

The great diffusional resistance of the stratum corneum has been demonstrated in a comparative absorption of drugs, like hydrocortisone. The mucous membranes in the rectal and vaginal regions permit the absorption of 26–29% of the steroid applied, while less than 2% of the applied dose is absorbed through the skin.

Compounds which are known or reported to enhance the transdermal delivery of drugs include dimethyl sulfoxide (DMSO), polyethylene glycol monolaurate, alkyl lactams, and long-chain amides. Prior art patents of relevance to penetrating enhancers of physiologically active agents include U.S. Pat. Nos. 3,551,554 which describes dimethyl sulfoxide, U.S. Pat. No. 3,989,816 discloses 1-substituted azacycloheptane-2-one; U.S. Pat. No. 4,132,781 discloses a topical antibiotic plus 2-pyrrolidone or an n-lower alkyl-2-pyrrolidone, U.S. Pat. No. 4,017,641 also describes 2-pyrrolidone but with propylene glycol; others of interest are U.S. Pat. Nos. 3,903,256, 4,343,798, 4,046,886, 3,934,013; 4,070,462; 4,130,643, 4,130,667, 4,289,764; 4,070,462; 3,527,864, 3,535,422, 3,598,123, 3,952,099, 4,379,454, 4,286,592; 4,299,826; 4,314,557; 4,343,798; 4,335,115; 3,598,122; 4,405,616, 3,896,238, 3,472,931 and 4,557,934.

In U.S. Pat. No. 4,861,764 (Samour et al) certain 1,3-dioxolanes and 1,3-dioxanes are described as useful for enhancing the absorption of therapeutic agents through the skin.

It is also known that charged molecules may be transported across the skin utilizing iontophoresis. Iontophoresis is a process which induces an increased migration of ions or charged molecules in an electrolyte medium following the flow of electric current. The transport of the charged molecules is driven by the electric field established between the driving electrodes.

The technique was first conceived in 1908 when it was demonstrated that ions could be driven across the skin by means of an electric current. Numerous studies utilizing ophthalmological iontophoresis, cocaine and epinephrine iontophoresis for anesthesia were conducted. Because of tissue burning, electrical shocking of patients, and other technical problems from about 1921 to the early 1940's iontophoresis was virtually discarded while many uses were advanced, perhaps the widest use of iontophoresis up to recently is that of diagnosing cystic fibrosis by iontophoresing pilocarpine into the skin in order to obtain sufficient sweat for diagnosis.

The limitations of iontophoresis are governed by three significant factors—safety, convenience and predictability. Many systems in the past have used household current to power the devices and these placed the patient in considerable shock hazard should the device malfunction. Also, the possibility of burns was a marked deterrent. A second generation of devices functioned with a constant voltage so that varying current levels, depending upon the impedance of the body tissue being treated were generated; thus, although the possibility of direct electric shock was limited, the change of burning tissues remained, primarily because burns will result if the current density becomes too high. If a small area of tissue is burned, the resistance or impedance of this same tissue decreases and, with a constant voltage device, the current increases, thus compounding the problem. Also, constant voltage devices are not predictable as regards the amount of drug iontophoresed into any one region. Current varies inversely as the impedance of the tissue encountered and the actual quantity of the drug being iontophoresed is directly proportional to the current level, therefore, a frequent concern has been the repeatability of drug dosage in terms of quantity and rate of drug transfer with respect to time. Because of the limitations imposed by constant voltage controlled current devices evolved as the major delivery system in this field.

A fourth major factor which governs the use of iontophoresis is the ability to deliver adequate, clinically effective levels of active ingredient within the parameters of safety, convenience and predictability. Many drugs, particularly large molecules cannot be delivered in adequate levels without the need to use high current densities which can lead to the problems discussed above, in addition to the possibility of irreversible changes on the skin which may further limit drug dosage transmission and effectiveness.

PRIOR ART

We are not aware of any prior art that employs a water-insoluble stratum corneum-lipid modifier to enhance the effectiveness of iontophoretic delivery through the skin.

In an abstract of a paper by William I. Higuchi delivered in Washington, D.C. May 1–3, 1989 at the American Association of Pharmaceutical Scientists workshop it is stated that "systematic studies reveal . . . how chemical enhancers may work synergistically with iontophoresis to enhance transport of ions across the skin."

In a paper by Srinivasan, Higuchi, Sims, Glaneric and Beld published in the "Journal of Pharmaceutical Science" (Vol 78 No. 5; pages 370–375, May 1989) a pretreatment of hairless mouse skin with absolute alcohol (ethanol) prior to iontophoretic treatment is described as enhancing the permeability coefficient of the skin for insulin. The pretreatment is done by soaking the skin (both sides, i.e., the stratum corneum and the dermal underside in the alcohol contained in both chambers of the diffusion cell at 37° C. for 2 hours, removing the alcohol and the chambers then thoroughly rinsed with buffer solution (pH 8.0 isotonic phosphate buffered saline).

"Journal of Pharmaceutical Science" (Vol. 7.9 (7), pages 588–91, July 1990—Srinivasan, Higuchi & Behl), pretreatment with ethanol was used to enhance the in vitro transdermal iontophoretic flux of two polypeptides (MW 1209.4 & 1150.17).

Patents describing various transdermal devices and/or patches are U.S. Pat. Nos. 3,598,122, 3,598,123, 3,734,097, 4,474,570, 4,557,723, 4,622,031, 4,839,174 and 4,943,435.

DESCRIPTION OF THE INVENTION

Figure 1A:
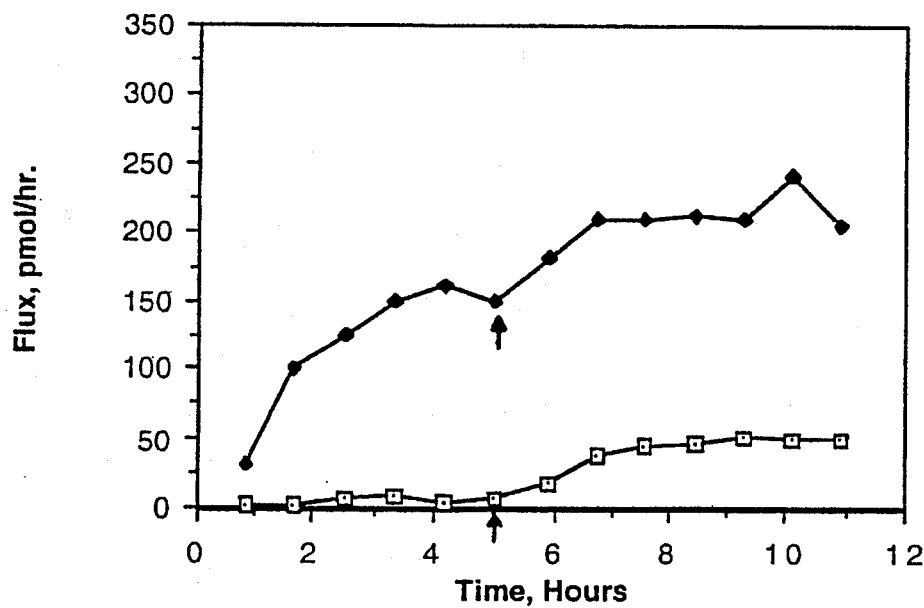
FIGS. 1A and 1B are graphical presentations of the data obtained in Example 1 and are plots of flux of active ingredient (pmol/hr) and concentration of active ingredient (pmol/ml), respectively, as a function of time (hour), for skin treated according to the invention (■), and skin not treated according to the invention (□).

It has been discovered that the use of certain water-insoluble (or substantially water-insoluble, i.e., "lipophilic") stratum corneum-lipid modifying agents vastly increase or enhance the amount of charged molecules which can be transported through the skin by iontophoresis. While many of these enhancers are known to increase the amount of many agents and in particular, physiologically active as well as non-physiologically active materials (e.g., humectants, softeners, and the like) in passive processes such as described in U.S. Pat. No. 4,861,764, it was unexpected that the stratum corneum-lipid modifiers herein disclosed and including those 1,3-dioxanes and 1,3-dioxolanes disclosed in aforementioned U.S. Pat. No. 4,861,764 would effect a vast increase in the flux of compounds and especially charged physiologically active agents deliverable through the skin by iontophoresis. The flux of the agent in a formulation containing the lipid modifier is much greater than one containing no lipid modifier. Among other things the degree of enhancement depends on the type and amount of lipid modifier and the chemical nature of the physiological active agent. The modification of the lipid layers in the stratum corneum using lipid modifiers permits the use of lower current densities for the same flux as that of unmodified skin. The lipid modifying agents mat be used as a pretreatment of the skin prior to iontophoresis (two step process) or, in another and preferred embodiment together with the agent to be administered (one step process).

The stratum corneum-lipid modifiers useful in this invention are water-insoluble or substantially water-insoluble compounds of the general formula: R—X wherein R may comprise in total a $C_5$ to $C_{28}$, preferably $C_7$ to $C_{16}$ and more preferably $C_8$ $C_{12}$ alkyl, including branched alkyl or unsaturated alkyl. The X group may be one of the following illustrative moieties; 1,3-dioxane; 1,3-dioxolane; a 5-, 6-, 7-, or 8- numbered lactam (e.g., butyrolactam, caprolactam, etc); morpholine; —COOH; —OH; cycloalkylene carbonate; —COOR'; —(OCH$_2$CH$_2$)$_n$—OH;

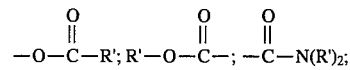

acetals

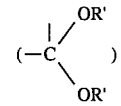

and hemicetals

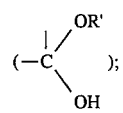

and wherein R' is a lower alkyl or an unsaturated lower alkyl (e.g. $C_1$ to $C_3$) and n is an integer from 1 to about 20.

Specific compounds within the above classes include, as illustrative only, 2-n-heptyl-1,3-dioxolane; 2-n-nonyl-1,3-dioxolane; 2-undecyl-1,3-dioxolane; pentylene-1,5-bis-1,3-dioxolane; 2-(2',6'-dimethyl-2',6',heptadienyl)-1,3-dioxolane; 2-n-nonyl-3-chloromethyl-1,3-dioxolane; 2-n-undecenyl-1,3-dioxane; 2-n-pentyl-5-(bis-ethylcarboxylate)-1,3-dioxane; n-tetradecyl alcohol; hexadecyl alcohol; n-octadecyl alcohol; oleic acid; stearic acid; methyl stearate; N,N'-dimethyl steramide; oleyl alcohol; N-decyl morpholine; N-dodecyl morpholine; decyl diethyl acetal; decanoyloxy cycloethylene carbonate; pentyl diethyl acetal; dodecyl methyl formate; 2-(2',6'-dimethyl-2', 6'-heptadienyl hemi- and di-methyl acetal; oleyl N,N-dimethyl formamide; dodecyl polyethylene glycol, wherein the number of ethylene oxide varies from 2 to 20; N-decyl pyrrolidone; N-dodecyl pyrrolidone; N-nonyl caprolactam; N-dodecyl caprolactam. The total number of carbon atoms in the lipid modifier compound should not be greater than about 50–60 carbon atoms.

In the compositions of this invention the amounts of the foregoing lipid modifier compounds may vary from about 0.5 wt. % to about 90 or more wt. %. In the two step process, the lipid modifier may be used as 100% active (i.e., when liquid) or in solution, suspension, emulsion or gel form. Further the latter forms may be used as such or carried on or in a substrate such as a coated or impregnated web, foam, etc. When used as a coating on a substrate, the lipid modifier may be part (e.g., 0.5 to 90+ wt. %) of the coating with other adjuvants present including binders. The coating may conveniently be of an adhesive nature to provide for securement to the skin.

When the lipid modifier is used in solution, suspension, emulsion, gel, etc. form (i.e., other than in 100% active form), the concentration of the lipid modifier may vary from about 0.5 wt. % to about 90, 95, 99, or 99.5 wt. %, preferably from about 1 to 80 wt. %, and more preferably from about 5 to 60 wt. %. When the lipid modifier is present in an aqueous hydrogel (based on hydrophilic, generally cross-linked polymers, copolymers, interpolymers and block copolymers preferred lipid modifier concentrations may range from about 0.5 to about 30 wt. %, and more preferably from about 1.0 to about 20 wt. % and still more preferably from 2 to 15 wt. %. Suitable liquids for preparing the solutions, dispersions etc. include water, ethanol, propylene glycol, glycol ethers, esters, etc. and mixtures thereof as illustrative only of dermatologically and preferably pharmaceutically acceptable liquids.

In the one step process of the present invention, where the lipid modifier and the agent to be transdermally administered are used together, the concentration of the lipid modifier may vary similarly in the two step process, allowing, of course, for the transdermal treating agent, and the necessary conductive, aqueous medium required for the iontophoretic technique.

In preferred forms of these compositions there is present a physiologically acceptable water-soluble organic polar compound, preferably liquid. Suitable compounds include: alcohols (e.g., isopropyl alcohol); glycols (e.g., propylene glycol, polyethylene glycol); lactams (e.g., pyrrolidone, N-ethyl pyrrolidone, caprolactam urea and derivatives (e.g., cycloethylene urea); 1,3-dioxolanes and lower alkyl derivatives (e.g., 1,3-dioxolane, 2-methyl-1,3-dioxolane; 4-hydroxymethyl-1,3-dioxolane, 4-methyl-1,3-dioxolane); 1,3-dioxanes (e.g., 2-methyl-1,3-dioxane); morpholine and lower alkyl morpholine (e.g., N-methyl morpholine); N-dimethyl formamide; dimethyl sulfoxide; low molecular weight esters (e.g., methyl acetate, ethyl lactate); mono- and poly-saccharides, (e.g., glucose, sucrose); aminoacids (e.g., glycine); amino alcohols (e.g., diethanol amine, triethanol amine); low molecular weight amines (e.g., diethylamine); carbonates (e.g., cycloethylene carbonate), etc. Preferred among the polar compounds are: ethanol; propylene glycol; polyethylene glycol; pyrrolidone and N-ethyl pyrrolidone; N-hydroxyethyl pyrrolidone; 1,3-dioxolane; morpholine; ethyl acetate; urea; N-dimethyl formamide; cycloethylene carbonate and mixtures of the foregoing. These polar compounds may be used in both the one, and two step processes in amounts ranging up to about 99 wt. %, preferably up to 50 wt. % and more preferably up to about 20 wt. %, depending of course on the delivery system.

The amount of the active agent in the compositions and articles of this invention to be transdermally administered (e.g., pharmaceutical, cosmetic, etc.) will vary widely depending on its function, and/or its physiological action and the desired levels to be achieved in the sub-dermal layers and/or circulatory system within a desired and/or necessary time frame. Illustratively, in the case of pharmaceuticals the amounts present in the compositions of the present invention may vary from as little as about 0.01 wt. % to as high as 50 wt. %. Preferred concentrations in the compositions range from about 0.1 wt. % to about 30 wt. % and more preferred are amounts of from about 0.1 wt. % to about 20 wt. %.

Another way of expressing the compositions of this invention is in terms of the range of parts of (A) lipid modifier, (B) active agent and (C) polar solvent. Generally the ranges of (A), (B) and (C) in parts by weight are as follows:

(A) 1,000: (B) 1: (C) 0 to (A) 1: (B) 500: (C) 500.

Since the preferred compositions of this invention as used in the one step process are aqueous systems, the water content in these will generally be significant such that the transdermal iontophoretic delivery system containing the active agent, lipid modifier and polar compound if any, is conductive, to permit the normal iontophoretic delivery process to take place. Illustratively one may use 50 or more wt. % water in the composition.

Other ingredients may be used in the compositions of this invention such as inorganic and organic electrolyte as is conventional in iontophoretic procedures to increase, if necessary and/or desirable the current density at a given voltage. Other dermatologically and/or pharmaceutically acceptable adjuvants may be used in conventional amounts for their indicated purposes as, for example, emulsifiers (e.g., 0.01 wt % to about 10 wt %); anti-oxidants (e.g., 0.001% to about 1 or 2 wt %); anti-microbial, and other preservative agents (e.g., 0.0001% to about 5 wt %); buffering agents (amounts as necessary); etc.

As described above, the compositions are generally, and preferably, used in combination with a carrier or substrate to facilitate contact with the skin thereby providing the novel products of this invention. In such combinations, the compositions may comprise from as little as 10 wt. % of the total weight of the combination to as much as 50, 60, 70, 80, 90 or more wt. % of the combination. As in the case of the lipid modifier used in the two step process, in the one step process, the compositions are admirably suitable for incorporation into electrically conductive adhesive compositions (e.g., coatings) and especially hydrophilic adhesives, again, in amounts of from about 10 wt. % to about 90 wt. % based on the weight of adhesive and the active compositions of this invention.

An unique and especially useful combination involves a compartmented adhesive product containing the lipid modifier in a hydrophilic pressure-sensitive adhesive with the active agent to be transdermally administered separated from the adhesive. In these combinations the preferred used polar compounds may be present with either or both of the separated components. The lipid modifier may be in encapsulated form to provide for continuous-control release characteristics. Transdermal patches useful in iontophoresis processes are described in U.S. Pat. Nos. 4,557,723, 4,474,570; 4,457,748; 4,325,367; 4,243,052; 4,141,359; 4,100,920;

4,066,078; 4,808,152; 4,622,031; 4,747,819; 4,786,277 and the compositions and processes of this invention may be applied using such patches.

The improved process embodying the present invention is demonstrated by the transport studies to follow: All transport studies are performed in side by side water jacketed, magnetically stirred and temperature controlled diffusion cells. Cell temperature is controlled to 37° C. by recirculating 37° water from a temperature controlled water bath through the water jacket. The volume of each half cell is 3.0 ml. The active skin area available for diffusion is 0.65 cm$^2$.

Most of the studies are performed in standard cells as obtained from Crown Glass, which have a single access port. Other studies use Crown Glass customized cells to allow for additional access ports to accommodate working electrodes, measuring electrodes and sampling access.

Full thickness dorsal skin is excised from 3–11 week old hairless mice (Charles River SKHI). Two skin samples are removed from each animal to form a matched pair. After excision, the skin is equilibrated in buffer solution (25 mM HEPES buffer in 0.1M NaCl adjusted to a pH of 7.4) for 12 hours at 4° C. to allow the skin to reach full hydration. Hydrated samples are examined to assess for gross morphological damage, and the dermal side is cleaned of any adhering subcutaneous tissue.

One of the two skin samples is treated with the lipid modifier compound by coating the epidermal side of the skin with the lipid modifier or a solution of the modifier in polar solvents. A two hour treatment period is allowed. After two hours, excess compound is removed from the surface of the skin by gently patting with an absorbent wipe. The modifier treated and the untreated skin samples are then mounted in identical diffusion cells filled with the HEPES buffer solution.

15 ul of $^{14}$C-indomethacin (New England Nuclear), corresponding to specific activity of 1.5 uCi is added to the chamber on the epidermal side of the skin (donor chamber). Samples from the receptor chamber are taken periodically by withdrawing 1 ml from the receptor compartment and replaced with fresh buffer at 37° C. The sampled solution is added to 18 ml of scintillation cocktail (Optiflour-Packard) and counted in a liquid scintillation counter.

After several hours of passive diffusion, a constant current is applied from the receptor side to the donor side of each diffusion cell by Ag/AgCl wire electrodes located in the respective compartments. The pH of the compartments is monitored and does not change significantly throughout the period of time when current is flowing. Samples are withdrawn from the receptor side periodically as described previously for an additional several hours.

The following examples will serve to illustrate the present invention without being deemed limitative thereof. Parts, where given are by weight unless otherwise indicated.

EXAMPLE 1

Utilizing the procedure outlined previously and with cells having additional access ports, one of two skin samples is treated with 2-n-nonyl-1,3-dioxolane lipid modifier by coating the epidermal side of the skin with the liquid lipid modifier. After 2 hours, excess liquid is removed from the surface of the skin by gently patting with an absorbent wipe. The treated and untreated skin samples are then mounted in identical diffusion cells filled with HEPES buffer solution. 15 ul of $^{14}$C-indomethacin (New England Nuclear), corresponding to an activity of 1.5 uCi is added to the chamber on the epidermal side of the skin (donor chamber). Samples from the receptor chamber are taken periodically by withdrawing 1 ml from the receptor compartment and replacing with fresh buffer at 37° C. The sampled solution is added to 18 ml of scintillation cocktail (Optifluor-Packard) and counted in a liquid scintillation counter.

Figure 1B:
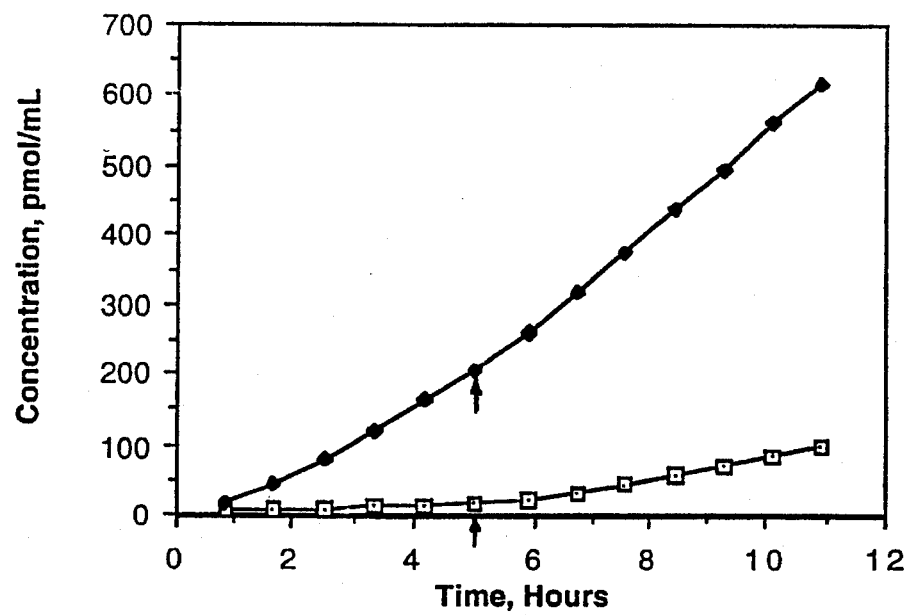
Figure 2A:
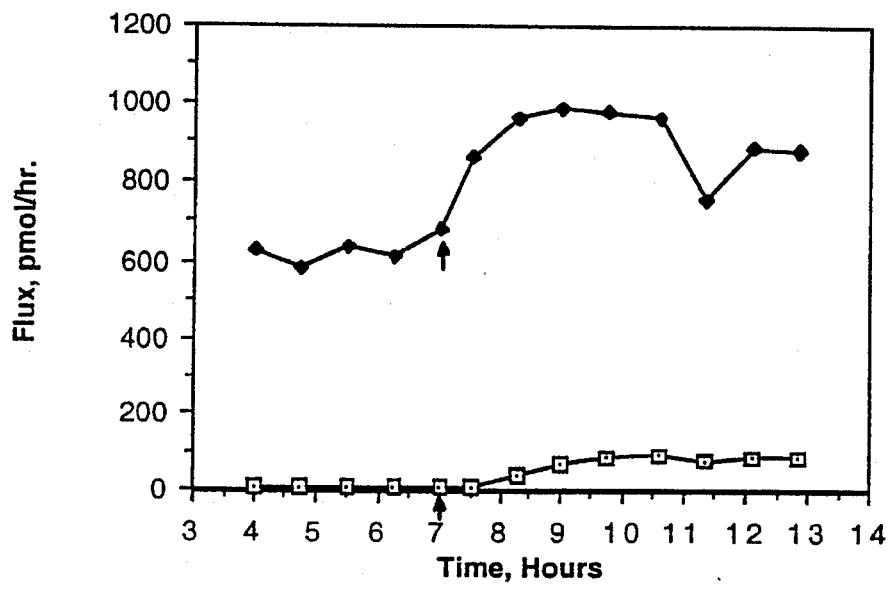
FIGS. 2A, 3A, 4A, 5A, 6A, 7A, 8A and 9A, are, similarly, plots of flux of active ingredient as a function of time.
Figure 2B:
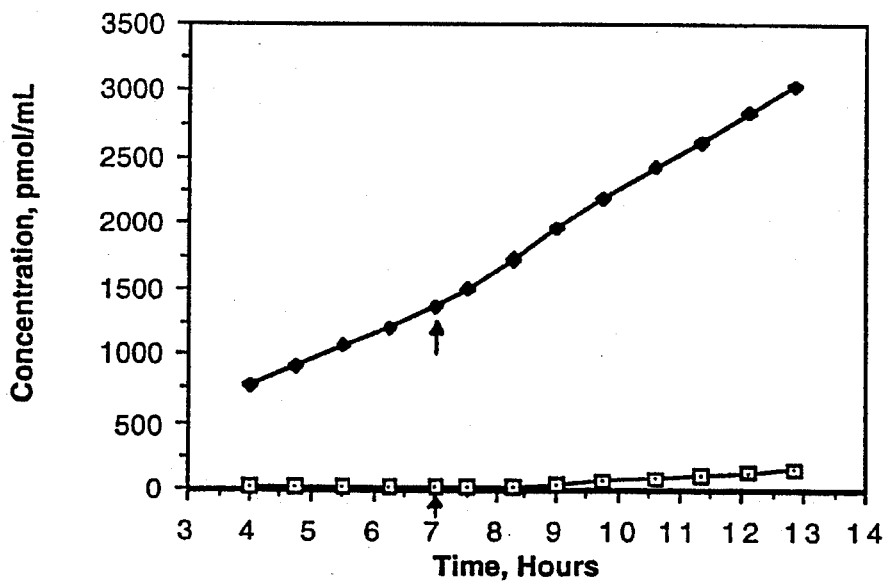
FIGS. 2B, 3B, 4B, 5B, 6B, 7B, 8B and 9B are similarly, plots of concentration of active ingredient, as a function of time; for skin treated with both lipid modifier and iontophoretic current (■) or with only iontophoretic current (□), for Examples 2–9, respectively.
Figure 3A:
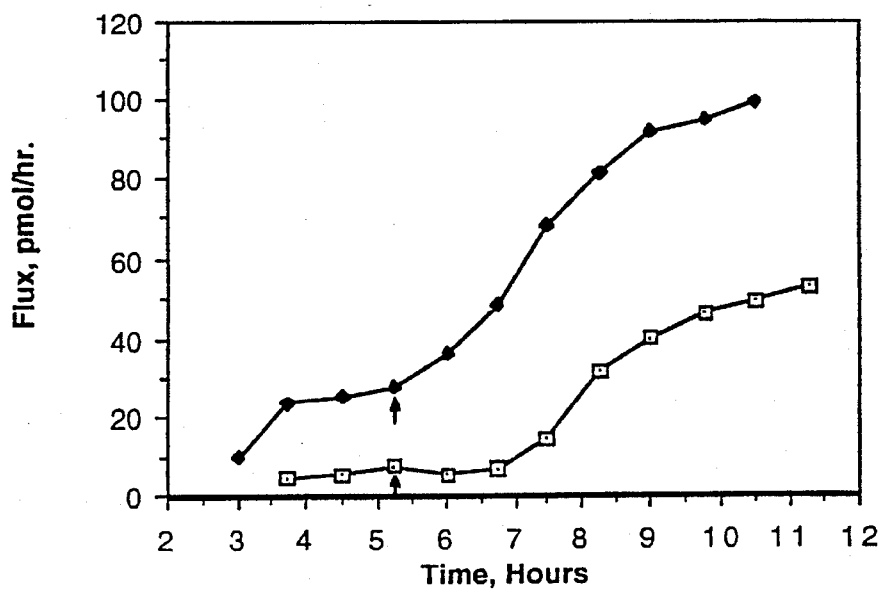
Figure 3B:
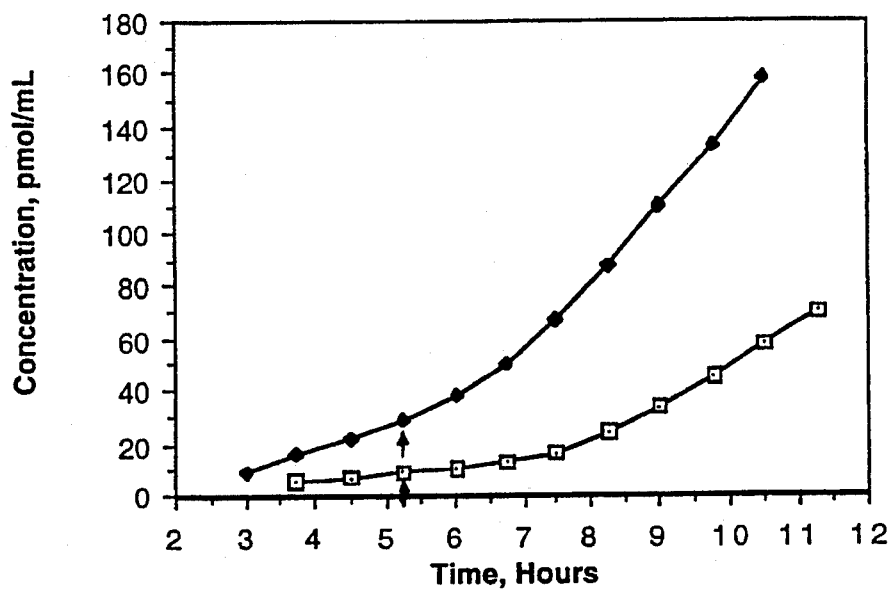
Figure 4A:
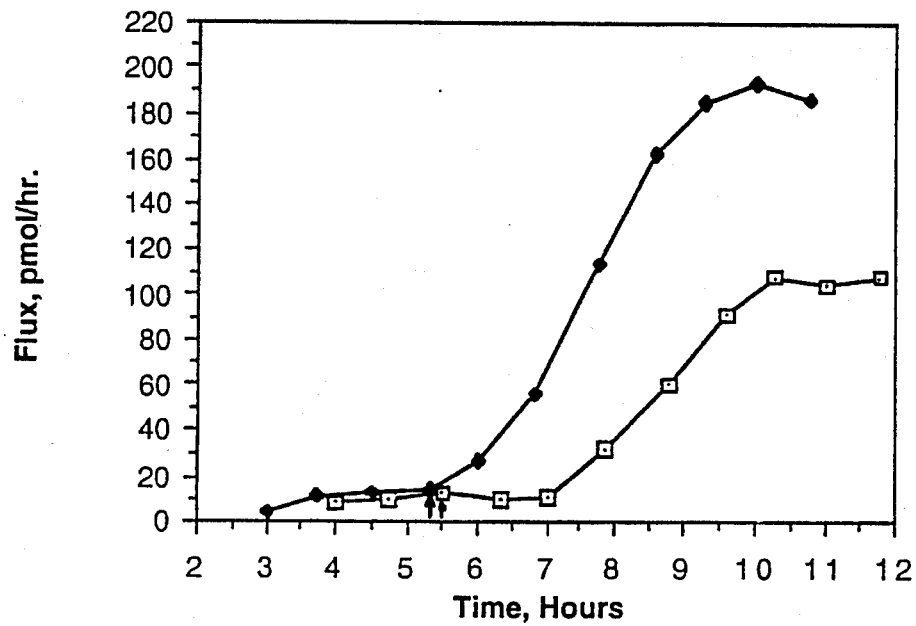
Figure 4B:
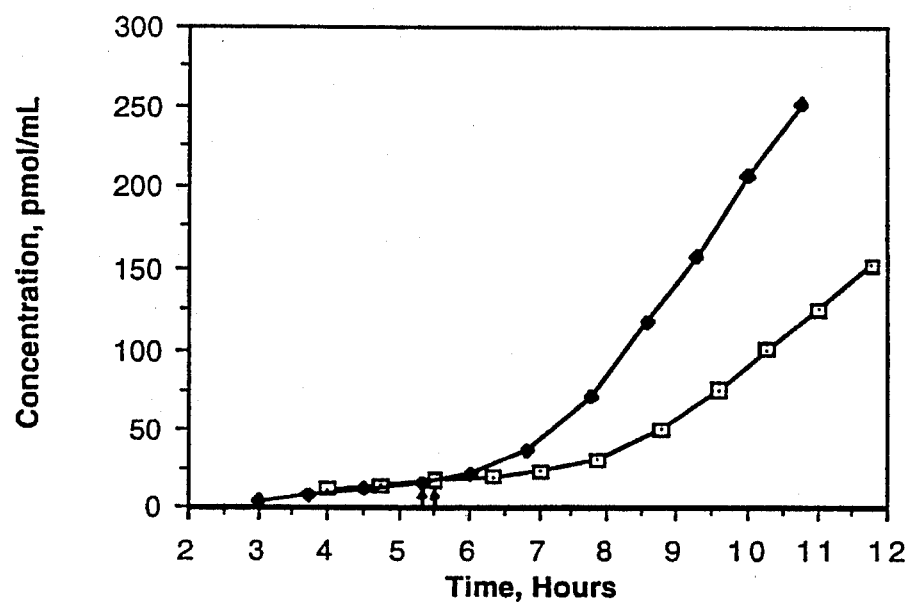
Figure 5A:
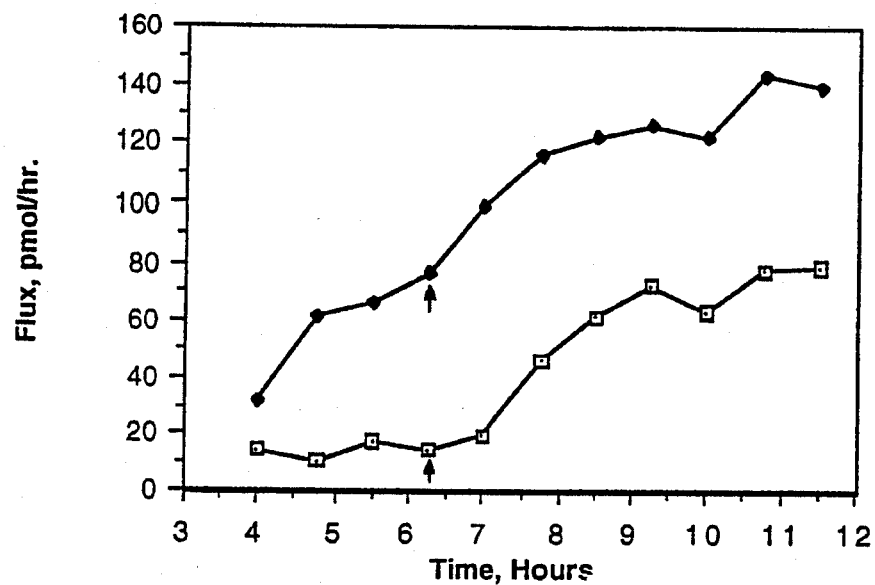
Figure 5B:
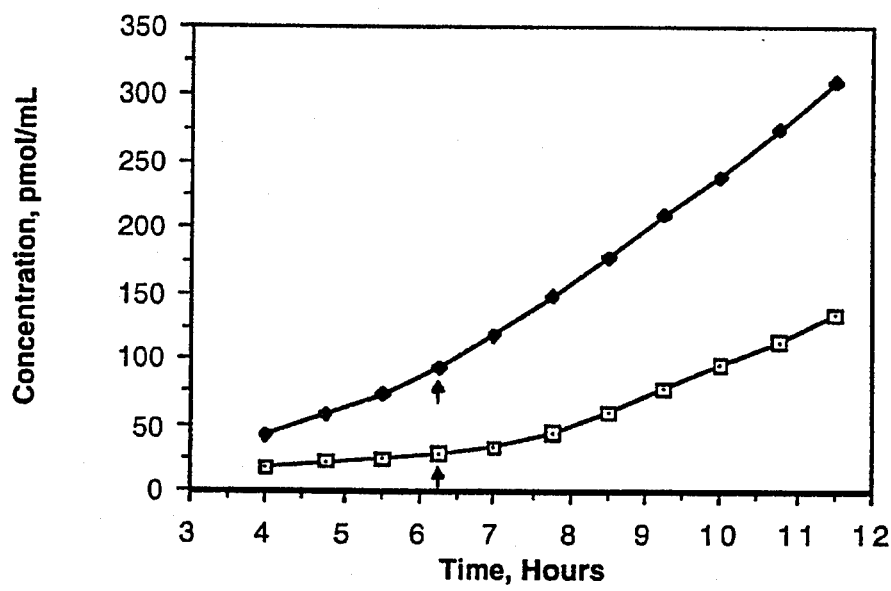
Figure 6A:
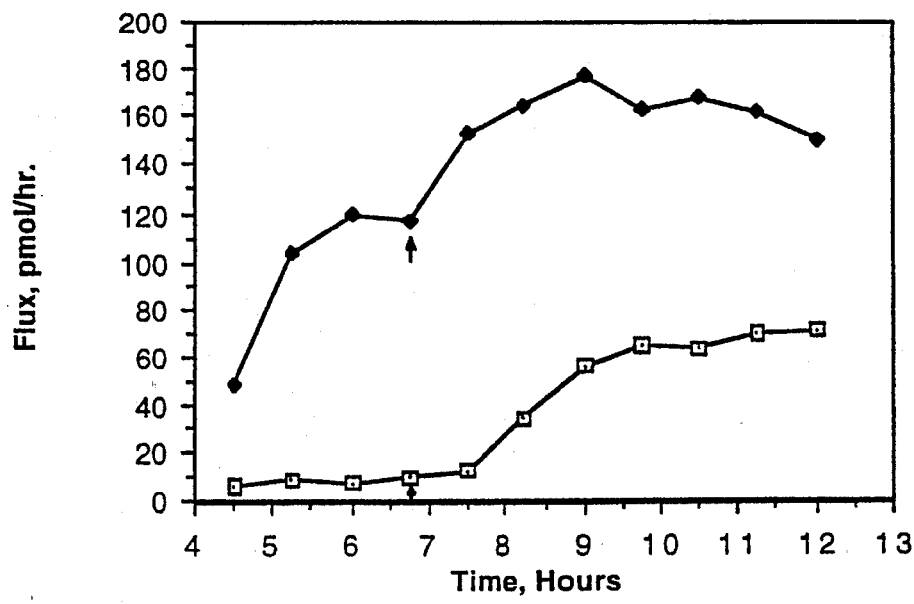
Figure 6B:
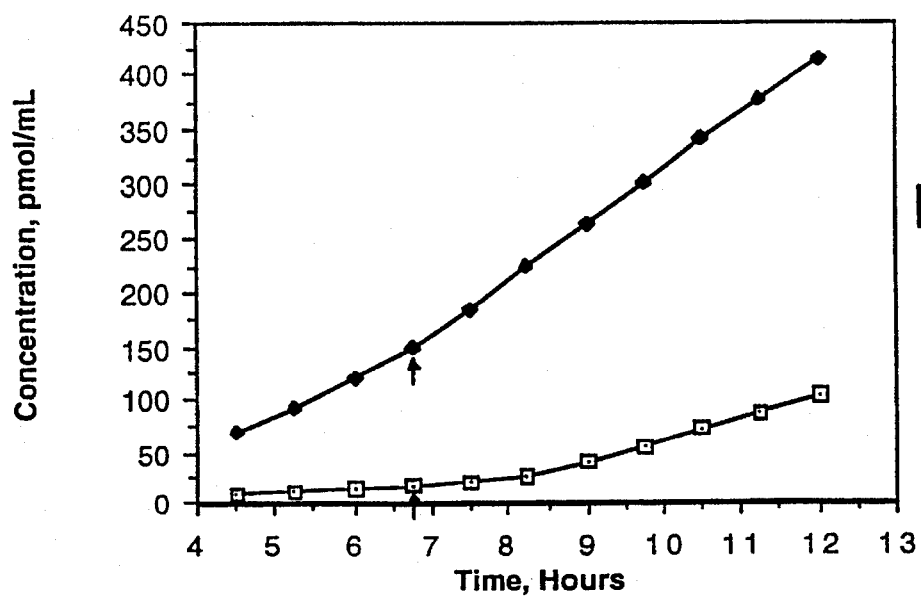
Figure 7A:
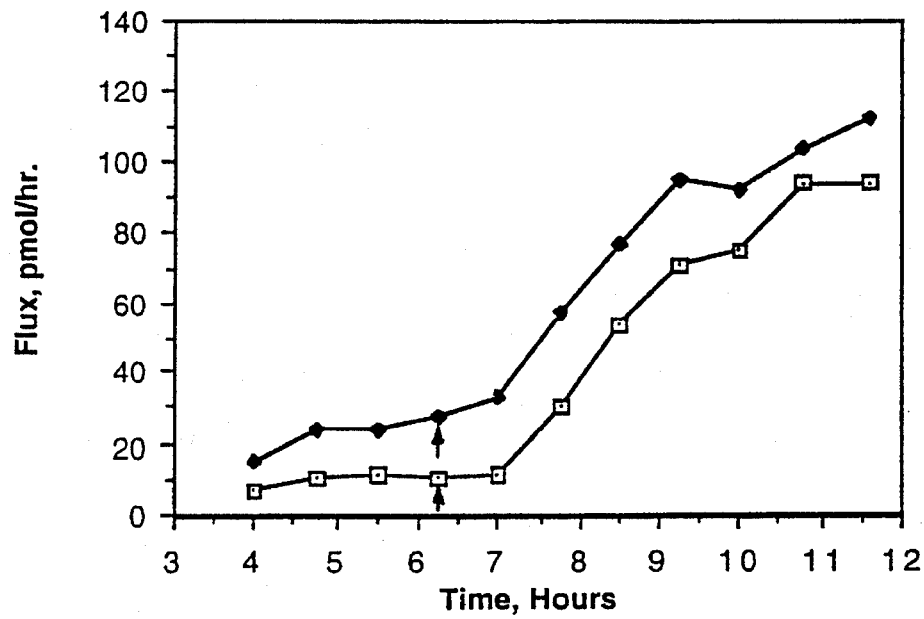
Figure 7B:
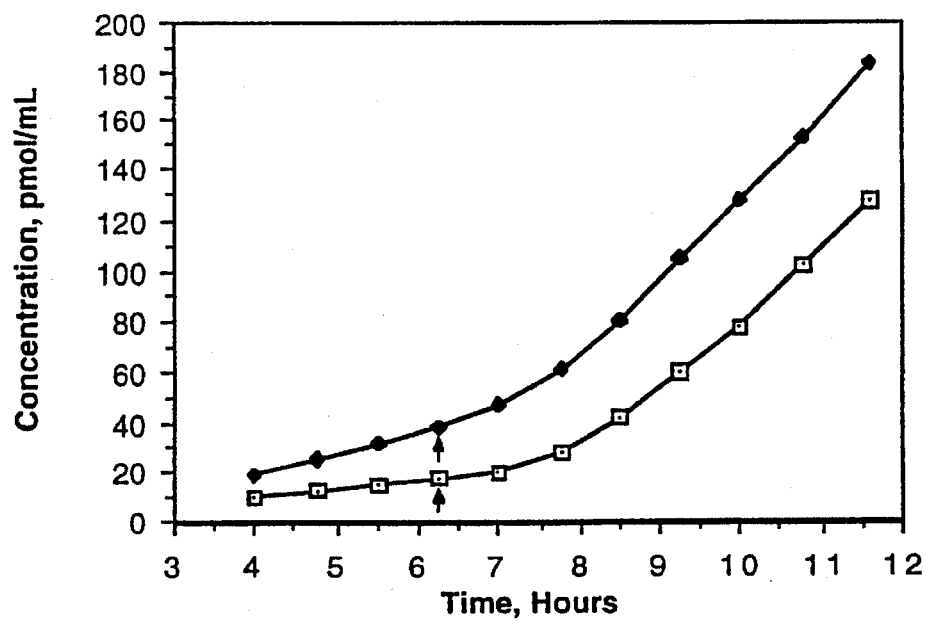
Figure 8A:
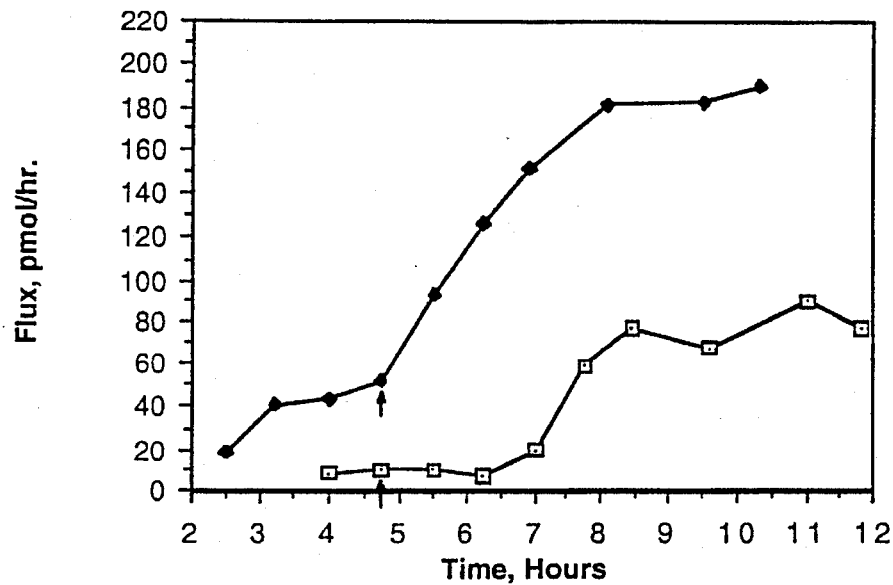
Figure 8B:
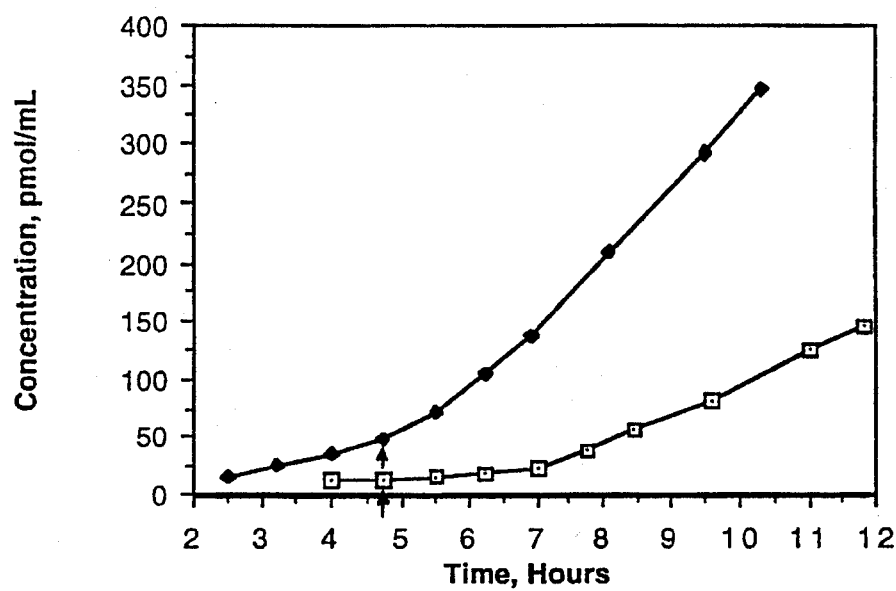
Figure 9A:
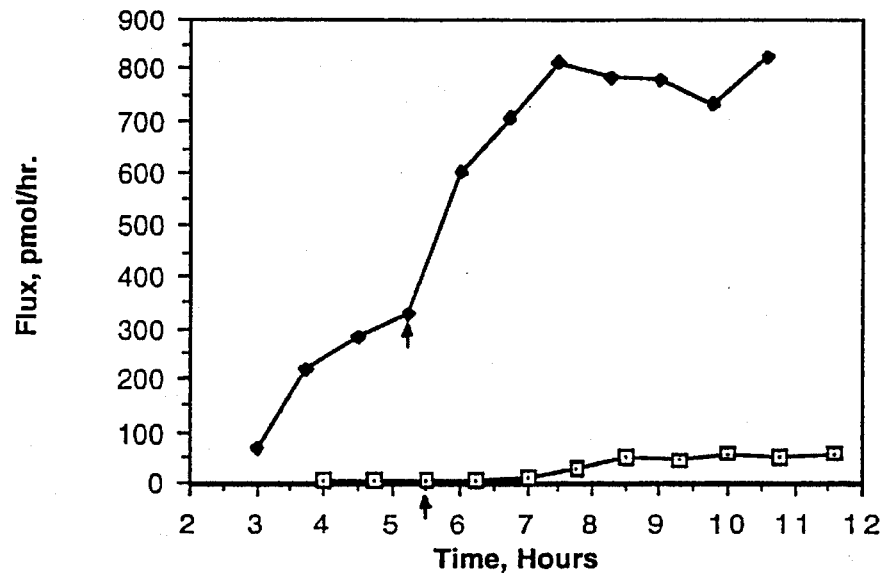
Figure 9B:
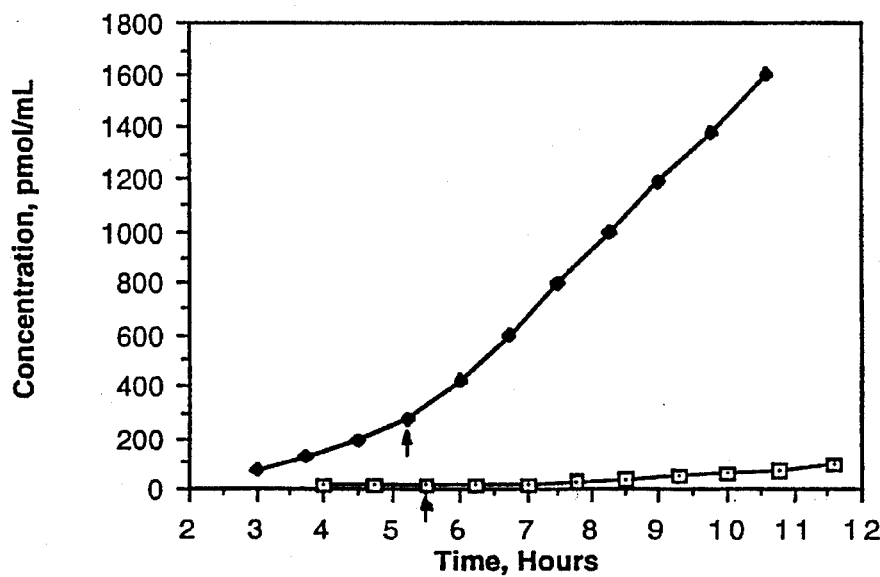
Figure 10A:
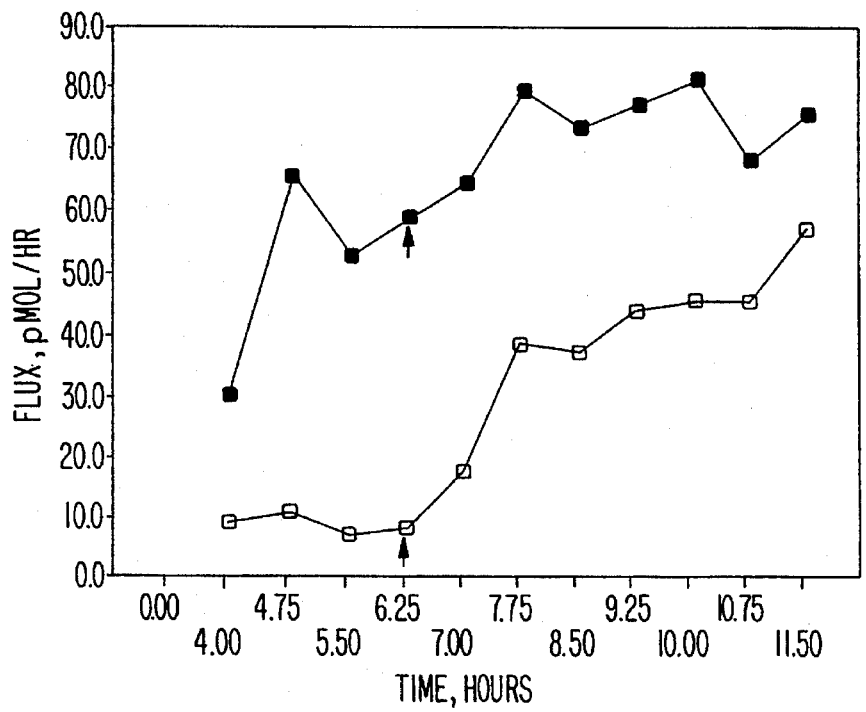
FIGS. 10A and 10B and 11A and 11B are also graphs plotting the flux (10A, 11A) and concentration (10B, 11B) of active ingredient as a function of time for Examples 10 and 11, respectively, for treated (■) and untreated (□) skin.
Figure 10B:
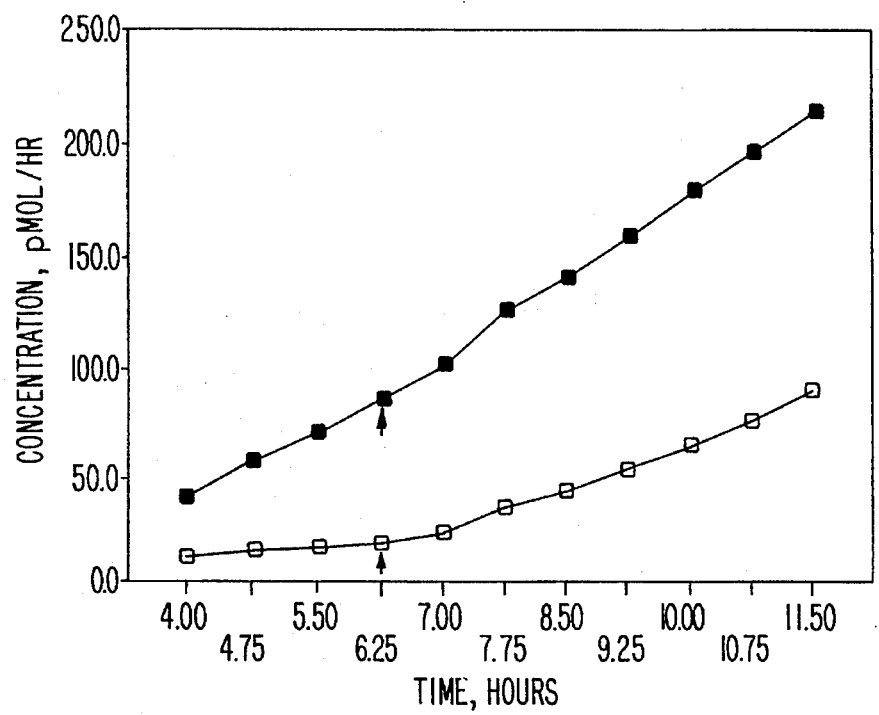
Figure 11A:
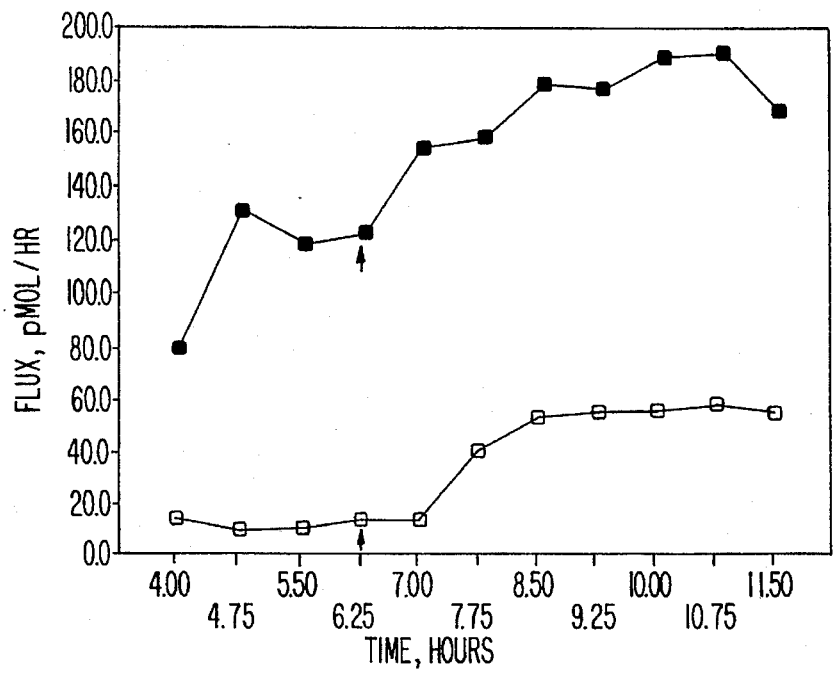
Figure 11B:
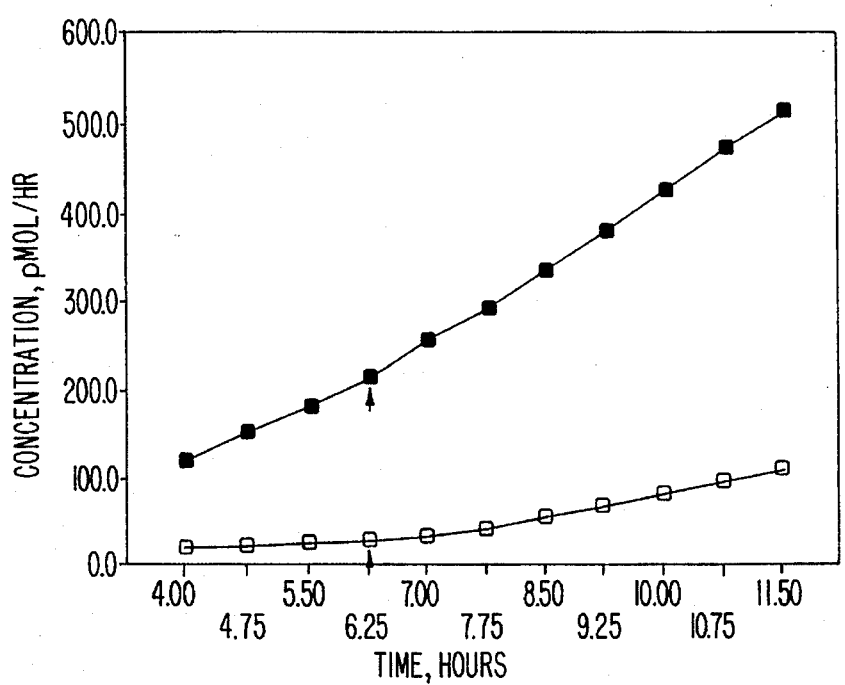

After 5 hours of passive diffusion (i.e., no iontophoretic current) a constant current of 0.32 mA (corresponding to 0.5 mA/cm$^2$) is applied from the receptor side to the donor side of each cell by Ag/AgCl wire electrodes located in the respective compartments. The pH of the compartments is monitored (and noted not to change significantly throughout the time that current is flowing). Samples are withdrawn from the receptor side periodically as described above for 6 additional hours. The flux values (p mol/hour) (p=pico) and the total picomols amount of indomethacin are measured. The results are tabulated below in Table 1 and graphically represented in FIG. 1A (flux data) and FIG. 1B (concentration data) for the untreated (□) and treated (■) skin.

TABLE I

Raw Data for Example 1

| Time, hrs | Untreated | | Treated | |
|---|---|---|---|---|
| | Flux* | Conc+ | Flux* | Conc+ |
| 0.83 | 2.8 | 7.7 | 31.4 | 15.8 |
| 1.67 | 1.8 | 8.2 | 100.6 | 43.7 |
| 2.50 | 6.7 | 10.1 | 125.1 | 78.5 |
| 3.33 | 9.9 | 12.8 | 149.1 | 119.9 |
| 4.17 | 4.9 | 14.2 | 159.5 | 164.2 |
| 5.00** | 5.8 | 15.8 | 149.5 | 205.7 |
| 5.92 | 18.6 | 21.5 | 179.6 | 260.6 |
| 6.75 | 37.7 | 32.0 | 208.7 | 318.6 |
| 7.58 | 45.6 | 44.6 | 208.7 | 376.5 |
| 8.42 | 47.6 | 57.8 | 211.6 | 435.3 |
| 9.25 | 51.0 | 72.0 | 208.5 | 493.2 |
| 10.08 | 49.2 | 85.7 | 241.3 | 560.3 |
| 10.92 | 48.2 | 99.0 | 204.8 | 617.1 |

*Flux - pmol/hr.
+Conc. - pmol/ml
**Start of Iontophoretic current of 0.32 mA (0.5 mA/cm$^2$).

From the above data we can see that the indomethacin with no skin treatment and no current gives a flux of less than 10 p mol/hr and a concentration value of less than 14. With treated skin the flux reaches to about 150 before iontophoretic current and the concentration is about 200. Significantly with the application of current, the untreated skin flux value reaches around 50 but with the treated skin the flux reaches about 210; and the concentration of drug delivered, after current starts, rises to 617 p mol/ml for treated skin while the untreated skin delivers only 99 p mol/ml.

It is clearly established that by utilizing a stratum corneum-lipid modifier together with iontophoresis there has been an increase in the flux and a tremendous increase in the amount of drug delivered transdermally not only after many hours of combined treatment but in the early phases of the combined technique one can deliver very much larger amounts of drug (Compare at 1 hr after onset of current and at the 6th hour) than the sum of values for iontophoresis alone or the lipid modifier alone.

Another method for quantifying the transport results is to compare the ratio of the various fluxes. There are four ratios that can be examined. These are:

(1) the ratio of the passive flux for skin treated with lipid modifier to the passive flux for untreated skin: $(LM)_{PAS}$. This ratio quantifies the enhancement of the passive delivery rate achieved by the lipid modifier without any current;

(2) the ratio of the active flux for the lipid modifier-treated skin to the active flux for the untreated skin: $(LM)_{Active}$. This ratio quantifies the enhancement of the delivery rate produced by the combined effects of the lipid modifier (LM) with iontophoresis compared to iontophoresis alone;

(3) the ratio of the active flux to the passive flux for the lipid modifier-treated skin; $(IER)_{LM}$. This ratio quantifies the enhancement of the delivery rate achieved by the lipid modifier (LM) and iontophoresis compared to the lipid modifier (LM) alone; and (4) the ratio of the active flux to the passive flux for untreated skin; $(IER)_{Control}$. This ratio quantifies the enhancement of the delivery rate achieved by iontophoresis alone.

The average of these values for 9 repeats of Example I are:

|  | Ave. ± SD* |
| --- | --- |
| $(IER)_{Control}$ = | 8.7 ± 2.1 |
| $(IER)_{LM}$ = | 2.3 ± 1.9 |
| $(LM)_{Pas}$ = | 23 ± 1.8 |
| $(LM)_{Active}$ = | 4.6 ± 2.7 |

*SD = Standard Deviation (n = 9)

The product of $(IER)_{Control}$ and $(LM)_{Active}$ or $(IER)_{LM}$ and $(LM)_{Pas}$ shows that the combined effect of the lipid modifier and iontophoresis produces a flux that is about 40 to 50 times larger than the diffusive flux across untreated skin.

EXAMPLE 2

Example I is repeated using however as the lipid modifier, N-n-dodecyl pyrrolidone. The enhancement ratios are

|  | Ave. ± SD (n = 2) |
| --- | --- |
| $(IER)_{Cntl}$ = | 11 ± 1.9 |
| $(IER)_{LM}$ = | 1.4 ± 0.4 |
| $(LM)_{Pas}$ = | 152 ± 73 |
| $(LM)_{Active}$ = | 18 ± 0.8 |

In this Example 2, the iontophoresis current is turned on after 7 hours and continued for 6 hours (instead of 5 hours as in Example 1). For untreated skin the passive flux for untreated skin is less than 10, without current. One and a half hours after the current is begun, the flux is about 40 p mol/hour. This flux levels off to about 80 p mol/hour until the 13th hour. For LM-treated skin the passive flux (i.e. no current) averages (from hours 4 to 7) about 600 p mol/hour and rises abruptly at the onset of current to almost 900 p mol/hour.

Examining the concentration of indomethacin delivered (p mol/ml), with the untreated skin, there was very little transport prior to current turn on (less than 20) and this reached about 145 p mol/ml (see the data for hours 10–13). The treated skin (without current) transported about 800 p mol/ml after 4 hours reaching a total of about 1400 p mol/ml and then with current on, there was an increase to reach a total of about over 3,000 p mol/ml at around the 13th hours.

The rate of delivery (flux) in the lipid modifier treated skin goes from around 600 p mol/hr to around 900 p mol/hr after applying the current, notwithstanding the fact that current alone gives a flux increase of only 80 p mol/hr.

The flux ratios $(IER)_{CONTROL}$; $(IER)_{LM}$; $(LM)_{PAS}$ & $(LM)_{ACTIVE}$ are shown in Table II.

EXAMPLE 3–9

Example I is again repeated using the following lipid modifiers in lieu of 2-n-nonyl-1,-3-dioxolane.

| Example | Lipid Modifier |
| --- | --- |
| 3 | 2-n-(2,6-Dimethyl-5-heptenyl)-1,3-dioxolane |
| 4 | 3-n-Decanoyloxy-1,3-propylene carbonate |
| 5 | 2-(9-n-Decenyl)-1,3-diaxolane |
| 6 | 2-Nonyl-1,3-dioxane |
| 7 | 2-Pentyl-1,3-dioxolane |
| 8 | 2-Nonyl-4-methyl-1,3-dioxolane |
| 9 | N-n-Dodecyl-ε-caprolactam |

The flux ratios (enhancement ratios) are also set out in Table II.

TABLE II

SUMMARY OF ENHANCEMENT RATIOS
(FLUX RATIOS)
FOR LIPID MODIFIERS OF EXAMPLE 2 TO 9

| Lipid Modifier of | $(IER)_{Cntrl}$ Ave. ± SD | $(IER)_{LM}$ Ave. ± SD | $(LM)_{Pas}$ Ave. ± 50 | $(LM)_{Active}$ Ave. ± SD |
| --- | --- | --- | --- | --- |
| Ex 2 | 11.0 ± 1.9 | 1.4 ± 0.4 | 152.0 ± 73.0 | 18.0 ± 0.8 |
| 3 | 9.2 ± 1.7 | 2.7 ± 1.6 | 9.9 ± 7.7 | 2.3 ± 0.2 |
| 4 | 9.0 ± 1.3 | 12.0 ± 4.6 | 1.1 ± 0.1 | 1.4 ± 0.4 |
| 5 | 6.1 ± 1.3 | 2.0 ± 0.3 | 7.9 ± 3.9 | 2.5 ± 1.1 |
| 6 | 6.9 ± 1.3 | 1.5 ± 0.1 | 14.0 ± 1.1 | 3.1 ± 0.8 |
| 7 | 11.0 ± 4.2 | 4.2 ± 0.1 | 2.5 ± 0.4 | 1.0 ± 0.8 |
| 8 | 9.2 ± 0.2 | 2.7 ± 2.1 | 12.0 ± 9.8 | 2.6 ± 0.1 |
| 9 | 14.0 ± 2.5 | 2.5 ± 0.7 | 110.0 ± 66.0 | 18.0 ± 3.0 |

The relevant flux and concentration raw data are shown below in Table III and in FIGS. 2A and 2B, 3A and 3B, 4A and 4B, 5A and 5B, 6A and 6B, 7A and 7B, 8A and 8B, and 9A and 9B, respectively for each of the lipid modifiers of Examples 2 to 9.

TABLE III

Raw Data for Examples 2–9

|  | Untreated | | Treated | |
| --- | --- | --- | --- | --- |
| Time, hrs. | Flux* | Conc+ | Flux* | Conc+ |
| | Example 2 | | | |
| 4.00 | 8.96 | 11.2 | 624.18 | 780.2 |
| 4.75 | 9.73 | 13.5 | 579.20 | 916.0 |
| 5.50 | 6.94 | 15.1 | 636.85 | 1065.2 |
| 6.25 | 9.04 | 17.2 | 608.01 | 1207.7 |
| 7.00** | 8.92 | 19.3 | 681.06 | 1367.4 |
| 7.50 | 10.22 | 20.9 | 861.67 | 1502.0 |
| 8.25 | 41.49 | 30.6 | 960.79 | 1727.2 |
| 9.00 | 66.17 | 46.1 | 984.85 | 1958.0 |
| 9.75 | 81.05 | 65.1 | 975.84 | 2186.7 |
| 10.58 | 90.57 | 88.7 | 964.62 | 2437.9 |
| 11.33 | 74.47 | 106.2 | 755.02 | 2614.9 |
| 12.08 | 83.77 | 125.8 | 890.42 | 2823.6 |
| 12.83 | 83.07 | 145.3 | 879.95 | 3029.8 |
| | Example 3 | | | |
| 3.00 | — | — | 9.58 | 9.6 |
| 3.75 | 4.76 | 5.9 | 23.64 | 15.5 |
| 4.50 | 5.13 | 7.2 | 25.08 | 21.8 |
| 5.25** | 7.60 | 9.1 | 27.48 | 28.6 |
| 6.00 | 5.69 | 10.6 | 35.67 | 37.6 |
| 6.75 | 6.91 | 12.3 | 48.07 | 49.6 |
| 7.50 | 14.32 | 15.9 | 68.15 | 66.6 |
| 8.25 | 31.71 | 23.8 | 81.01 | 86.9 |
| 9.00 | 39.91 | 33.8 | 91.85 | 109.8 |

TABLE III-continued

Raw Data for Examples 2–9

| 9.75 | 45.52 | 45.1 | 94.83 | 133.5 |
| 10.50 | 48.63 | 57.3 | 99.45 | 158.4 |
| 11.25 | 52.45 | 70.4 | — | — |

| | Untreated | | Treated | |
| --- | --- | --- | --- | --- |
| Time, hrs. | Flux* | Conc+ | Time, hrs. Flux* | Conc+ |

Example 4

| 4.00 | 8.63 | 11.6 | 3.00 | 4.68 | 4.7 |
| 4.75 | 9.86 | 14.0 | 3.75 | 11.36 | 7.5 |
| 5.50** | 12.23 | 17.1 | 4.5 | 12.55 | 10.7 |
| 6.33 | 9.98 | 19.9 | 5.33** | 14.12 | 14.6 |
| 7.00 | 11.72 | 22.5 | 6.00 | 26.22 | 20.4 |
| 7.83 | 32.38 | 31.5 | 6.83 | 56.52 | 36.1 |
| 8.75 | 60.25 | 49.9 | 7.75 | 113.48 | 70.8 |
| 9.58 | 91.56 | 75.3 | 8.58 | 162.72 | 116.0 |
| 10.25 | 107.68 | 99.2 | 9.25 | 185.53 | 157.2 |
| 11.00 | 103.14 | 125.0 | 10.00 | 193.71 | 205.6 |
| 11.75 | 107.43 | 151.9 | 10.75 | 187.01 | 252.4 |

| | Untreated | | Treated | |
| --- | --- | --- | --- | --- |
| Time, hrs. | Flux* | Conc+ | Flux* | Conc+ |

Example 5

| 4.00 | 14.00 | 18.7 | 31.56 | 42.0 |
| 4.75 | 10.57 | 21.3 | 61.04 | 57.3 |
| 5.50 | 16.87 | 25.5 | 65.80 | 73.8 |
| 6.25** | 14.36 | 29.1 | 76.85 | 93.0 |
| 7.00 | 19.18 | 33.9 | 98.89 | 117.7 |
| 7.75 | 46.15 | 45.5 | 116.01 | 146.7 |
| 8.50 | 61.50 | 60.8 | 121.96 | 177.2 |
| 9.25 | 72.53 | 79.0 | 126.16 | 208.8 |
| 10.00 | 63.30 | 94.8 | 122.09 | 239.3 |
| 10.75 | 77.47 | 114.2 | 143.21 | 275.1 |
| 11.50 | 78.59 | 133.8 | 139.60 | 310.0 |

Example 6

| 4.50 | 6.79 | 9.5 | 48.45 | 68.1 |
| 5.25 | 8.83 | 11.6 | 102.93 | 92.3 |
| 6.00 | 8.23 | 13.5 | 120.37 | 120.5 |
| 6.75** | 10.73 | 16.1 | 117.28 | 148.0 |
| 7.50 | 12.77 | 19.1 | 153.23 | 183.9 |
| 8.25 | 34.91 | 27.2 | 164.78 | 222.5 |
| 9.00 | 55.93 | 40.3 | 176.55 | 263.9 |
| 9.75 | 64.67 | 55.5 | 162.51 | 302.0 |
| 10.50 | 63.30 | 70.3 | 168.66 | 341.5 |
| 11.25 | 69.71 | 86.7 | 162.29 | 379.5 |
| 12.00 | 70.95 | 103.3 | 150.90 | 414.9 |

Example 7

| 4.00 | 7.36 | 9.8 | 14.76 | 19.7 |
| 4.75 | 10.80 | 12.5 | 23.87 | 25.6 |
| 5.50 | 11.50 | 15.4 | 24.22 | 31.7 |
| 6.25** | 10.56 | 18.0 | 27.56 | 38.6 |
| 7.00 | 11.87 | 21.0 | 33.06 | 46.9 |
| 7.75 | 30.02 | 28.5 | 57.43 | 61.2 |
| 8.50 | 53.21 | 41.8 | 76.95 | 80.5 |
| 9.25 | 70.50 | 59.4 | 94.66 | 104.1 |
| 10.00 | 75.14 | 78.2 | 92.07 | 127.1 |
| 10.75 | 93.89 | 101.7 | 103.00 | 152.9 |
| 11.58 | 93.37 | 127.6 | 111.98 | 184.0 |

| Time, hrs. | Flux* | Conc+ | Time, hrs. | Flux* | Conc+ |
| --- | --- | --- | --- | --- | --- |

Example 8

| 4.00 | 8.61 | 11.5 | 2.50 | 18.83 | 15.7 |
| 4.75** | 9.15 | 13.8 | 3.25 | 40.68 | 25.9 |
| 5.50 | 9.53 | 16.2 | 4.00 | 43.35 | 36.7 |
| 6.25 | 7.68 | 18.1 | 4.75** | 51.41 | 49.5 |
| 7.00 | 19.62 | 23.0 | 5.50 | 92.31 | 72.6 |
| 7.75 | 58.95 | 37.7 | 6.25 | 125.50 | 104.0 |
| 8.42 | 77.17 | 54.9 | 6.92 | 151.54 | 137.7 |
| 9.58 | 67.92 | 81.3 | 8.08 | 180.88 | 208.0 |

| 11.00 | 90.16 | 123.9 | 9.50 | 182.31 | 294.1 |
| 11.83 | 77.54 | 145.4 | 10.33 | 189.40 | 346.7 |

Example 9

| 4.00 | 5.58 | 7.4 | 3.00 | 68.20 | 68.2 |
| 4.75 | 4.37 | 8.5 | 3.75 | 217.97 | 122.7 |
| 5.50** | 5.39 | 9.9 | 4.50 | 281.42 | 193.0 |
| 6.25 | 4.02 | 10.9 | 5.25** | 324.35 | 274.1 |
| 7.00 | 9.77 | 13.3 | 6.00 | 602.82 | 424.8 |
| 7.75 | 31.38 | 21.2 | 6.75 | 705.91 | 601.3 |
| 8.50 | 50.33 | 33.8 | 7.50 | 812.22 | 804.4 |
| 9.25 | 45.74 | 45.2 | 8.25 | 786.65 | 1001.0 |
| 10.00 | 57.89 | 59.7 | 9.00 | 778.20 | 1195.6 |
| 10.75 | 50.89 | 72.4 | 9.75 | 734.20 | 1379.1 |
| 11.58 | 59.39 | 88.9 | 10.58 | 824.04 | 1608.0 |

*Flux - pmol/hr.
+Conc. - pmol/ml.
**Start of Iontophoretic current of 0.32 mA (0.5 mA/cm$^2$).

The following Table IV gives the flux values (p mol/hr) averaged for the total time shown on the graphs in FIGS. 1A to 9A for flux values and FIGS. 1B to 9B for concentration values.

TABLE IV

| | Controls (No Lipid Modifier) | | Treated Skin (Lipid Modifier Added) | |
| --- | --- | --- | --- | --- |
| Ex. | No Current | Current | No Current | Current On |
| 1 | 6 | 50 | 150 | 210 |
| 2 | 9 | 80 | 600 | 900 |
| 3 | 7 | 50 | 25 | 95 |
| 4 | 10 | 100 | 10 | 190 |
| 5 | 14 | 75 | 65 | 130 |
| 6 | 8 | 70 | 120 | 165 |
| 7 | 10 | 90 | 25 | 100 |
| 8 | 10 | 80 | 40 | 180 |
| 9 | 5 | 55 | 240 | 780 |

EXAMPLES 10 & 11

The results of studies conducted on indomethacin as the active agent using polar water-soluble compounds are shown in the graphs of FIGS. 10A and 10B and FIGS. 11A and 11B. Solutions of 2% and 10% of 2-n-nonyl-1,3-dioxolane in a mixture of propylene glycol and ethanol (1:1, V/V) are used in enhancing the iontophoretic delivery of indomethacin. Similar observations of increased flux and concentration of the active agent in the receptor cell are observed. The results show that indomethacin enhancement is in the following order—100% lipid modifier>10%>2%.

The graphs for the relevant fluxes and concentrations of examples 1 to 11 are shown in the accompanying figures. The solid squares refer to treated skin and the open squares to untreated skin. The symbol ↑ refers to the time the iontophoretic current is applied.

We claim:

1. A biocompatible composition suitable for iontophoretic administration to an animal host through the skin thereof comprising a pharmaceutically acceptable agent to be administered and a pharmaceutically acceptable water insoluble transdermal penetration enhancing compound selected from the group consisting of $C_7$ to $C_{16}$ aliphatic group substituted acetals, hemi-acetals and morpholines and further comprising a physiologically acceptable water-soluble polar compound selected from the group consisting of alcohols, glycols, lactams, urea, cycloethylene urea, 1,3-dioxolane, 2-methyl-1,3-dioxolane, 4-hydroxymethyl- 1,3-dioxolane, 4-methyl-1,3-dioxolane, 1,3-dioxane, 2-methyl-1,3-dioxane, morpholine, N-methylmorpholine, N-dimethylformamide, dimethylsulfoxide, methylacetate, ethyllactate, monosaccharides, polysaccharides, amino acids, amino alcohols, diethylamine and cycloethylene carbonate.

2. A composition as defined in claim 1 wherein the polar compound is selected from the group consisting of alcohol, glycol, lactam, dioxolane, formamide, carbonate, glucose, urea and mixtures thereof.

3. A composition as defined in claim 2 wherein the polar compound is an alcohol glycol mixture.

4. A composition as defined in claim 2 wherein the polar compound is a lactam.

5. In a transdermal patch for use in the iontophoretic administration of an active ingredient through animal skin and comprising an active ingredient in combination with a conductive adhesive adapted to be secured to the skin, the improvement wherein said adhesive contains an effective amount of a dermatologically and/or pharmaceutically acceptable substantially water-insoluble transdermal penetration enhancing compound selected from the group consisting of acetals, hemi-acetals and morpholines wherein the lipid modifier contains a $C_5$ to $C_{28}$ aliphatic group and the total number of carbon atoms in the transdermal penetration enhancing compound is not greater than about 60 carbon atoms.

6. In a patch as defined in claim 5, wherein the adhesive comprises a layer separate from the active agent.

7. In a method for the administration of an active agent through the skin of an animal host by iontophoresis, the improvement which comprises applying to the skin at the same time as the agent is applied, a substantially water-insoluble transdermal penetration enhancing compound selected from the group consisting of acetals, hemi-acetals and morpholines wherein the lipid modifier contains a $C_5$ to $C_{28}$ aliphatic group and the total number of carbon atoms in the lipid modifier compound is not greater than about 60 carbon atoms.

8. The method of claim 7, wherein the enhancing compound is said 1,3-dioxane or 1,3-dioxolane.

9. The method of claim 7, wherein the enhancing compound is said acetal or hemi-acetal.

10. The method of claim 7, wherein the enhancing compound is said morpholine.

11. The method of claim 7 wherein the $C_5$ to $C_{28}$ aliphatic moiety is alkyl or unsaturated alkyl or substituted form thereof.

12. The method of claim 7 wherein the aliphatic moiety is a $C_7$ to $C_{16}$ saturated or unsaturated alkyl.

13. In a method for the administration of an active agent through the skin of an animal host by iontophoresis, the improvement which comprises first treating the skin in the absence of the agent with a transdermal penetration enhancing compound no more than about seven hours prior to the application of iontophoretic current in the absence of the agent, and thereafter applying iontophoretic current to the treated skin in the presence of the agent, said stratum-corneum-lipid modifier being selected from the group consisting of acetals, hemi-acetals and morpholines, wherein the lipid modifier is substantially water-insoluble and contains a $C_5$–$C_{28}$ aliphatic group and the total number of carbon atoms in the lipid modifier compound is not greater than about 60 carbon atoms.

14. The method of claim 13 wherein the $C_5$–$C_{28}$ aliphatic moiety is alkyl or unsaturated alkyl or substituted form thereof.

15. The method of claim 13 wherein the aliphatic moiety is a $C_7$–$C_{16}$ saturated or unsaturated alkyl.

16. The method of claim 15 wherein the enhancing compound is said acetal or hemi-acetal.

17. The method of claim 16 wherein the enhancing compound is decyl diethyl acetal.

18. The method of claim 15 wherein said enhancing compound is said morpholine.

19. The method of claim 13 wherein the skin is treated with the enhancing compound from about 1 minute to about 3 hours prior to application of iontophoretic current.

20. The method of claim 13 wherein the enhancing compound is applied to the skin from about 1 minute to about 30 minutes prior to the application of iontophoretic current.

* * * * *